(12) United States Patent
Brenneise

(10) Patent No.: US 8,371,310 B2
(45) Date of Patent: Feb. 12, 2013

(54) PORTABLE VAPORIZING DEVICE AND METHOD FOR INHALATION AND/OR AROMATHERAPY WITHOUT COMBUSTION

(76) Inventor: Jake Brenneise, Tucson, AZ (US)

( * ) Notice: Subject to any disclaimer, the term of this patent is extended or adjusted under 35 U.S.C. 154(b) by 453 days.

(21) Appl. No.: 12/279,837

(22) PCT Filed: Feb. 13, 2007

(86) PCT No.: PCT/US2007/062084
§ 371 (c)(1), (2), (4) Date: Jul. 19, 2010

(87) PCT Pub. No.: WO2007/098337
PCT Pub. Date: Aug. 30, 2007

(65) Prior Publication Data
US 2011/0120482 A1  May 26, 2011

Related U.S. Application Data

(60) Provisional application No. 60/774,723, filed on Feb. 17, 2006.

(51) Int. Cl.
*A24F 11/00* (2006.01)
*A24F 47/00* (2006.01)

(52) U.S. Cl. ........ 131/328; 131/194; 131/272; 131/273; 131/330

(58) Field of Classification Search .................. None
See application file for complete search history.

(56) References Cited

U.S. PATENT DOCUMENTS 3,877,842 A   4/1975   Greene et al.
6,095,153 A   8/2000   Kessler et al.

*Primary Examiner* — Richard Crispino
*Assistant Examiner* — Phu Nguyen
(74) *Attorney, Agent, or Firm* — Dale F. Regelman; Quarles & Brady LLP

(57) ABSTRACT

A hand-held apparatus (100) to vaporize volatile compounds disposed in a solid source material is disclosed. The hand-held apparatus comprises a housing (105), a mouthpiece tube (118) removeably disposed within, and extending outwardly from, said housing, a heating element assembly (114) in communication with said mouthpiece tube, wherein said heating element assembly heats to an operating temperature of about 450° F. in about 60 seconds.

7 Claims, 3 Drawing Sheets

PORTABLE VAPORIZING DEVICE AND METHOD FOR INHALATION AND/OR AROMATHERAPY WITHOUT COMBUSTION

CROSS-REFERENCE TO RELATED APPLICATION

This Application claims priority from a U.S. Provisional Application having Ser. No. 60/774,723 filed on Feb. 17, 2006.

FIELD OF THE INVENTION

This invention relates to smoking materials and methods, specifically a device for reducing the harm associated with the delivery of active ingredients and flavor compounds from tobacco and/or other plant materials or other source material(s).

BACKGROUND OF THE INVENTION

For centuries, maybe even millennia, people have burned plant material, such as for example tobacco leaves, in order to inhale the smoke to realize a physiologic effect from one or more compounds contained within that smoke. However, this burning process comprises a high temperature oxidation that produces many chemical compounds not present in the original material. Certain of those new compounds are unhealthful and/or carcinogenic.

Dried tobacco leaves, for instance, contain approximately 300 different chemical compounds, yet, when combusted, the resulting smoke contains approximately 5000 different compounds. Many of the oxidation products are known to be unhealthful, such as carbon monoxide (CO) and the family of polycyclic aromatic hydrocarbons (PAH's). In addition, in the elevated and uncontrolled temperature of combustion, many of the desirable compounds, such as nicotine, are destroyed. As a result, a large quantity of the original material is needed because much of the desired compound(s) are destroyed in the combustion process.

The desirable compounds in the smoke are not in fact created in the combustion process, but rather exist in the plant material in its natural state. The combustion process serves only to vaporize those desired compounds. A more healthful alternative to combusting the plant material as a means to release its active or desired constituents exists. Applicant's method heats plant matter to a temperature just below combustion temperature for cellulose of 450 degrees Fahrenheit, thereby generating an aerosol comprising the desired compounds.

U.S. Pat. No. 4,303,083 teaches an electrical device similar in appearance to an ordinary tobacco pipe in which the tobacco is placed directly in the electrically heated bowl, and the amount of heating is controlled by the setting of a variable resistance heater. The '083 patent illustrates the problem inherent with conductive heating, namely the non-uniform heating of the plant matter. The tobacco in direct contact with the heating element gets much hotter than other tobacco disposed farther from the heating element. Such non-uniform heating burns some of the tobacco, while at the same time inadequately heating other portions. In addition, the invention of the '083 patent is deficient because the amount of heat energy delivered will need to be adjusted based on varying inhalation rates.

U.S. Pat. No. 6,095,153 teaches a device which uses a heater to heat air to a selected temperature, and maintains that temperature within a narrow range. However, in order to maintain that narrow temperature range, the invention of the '153 patent necessarily comprises a large thermal mass, which requires a considerable warm-up time. In addition, such a large thermal mass results in an undesirable bulky and heavy apparatus, which adversely affects portability.

U.S. Pat. No. 6,513,524 teaches an apparatus for generating volatized vapor from different materials, and a way to collect and removeably distribute the gathered vapor. This device comprises a base unit which requires utility power, and is therefore, non-portable. In addition, the invention of the '524 patent is inconvenient to use because the user must manually set the amount of heat energy generated, meaning the user will have to go through a process of trial and error to determine the optimum setting. The device also requires considerable setup time, in waiting first for the unit to preheat, and then for a bag to fill with vapor and then cool.

U.S. Pat. No. 5,865,185 teaches a smoking article in which a replaceable tobacco flavor unit containing tobacco flavor material is electrically heated by a set of permanent reusable heaters to evolve flavors or other components in vapor or aerosol form for delivery to a smoker. Each heater heats only a portion of the available tobacco flavor material so that a plurality of individual puffs of tobacco flavor substance can be delivered sequentially to the smoker. This article makes no attempt to control or limit the temperature to which the tobacco is subjected, other than limiting the applied energy, which is applied in a conductive and radiative sense, and therefore stands a very high chance of delivering combustion products to the user, along with the tobacco flavor.

Accordingly, several objects and advantages of Applicant's invention are the following: more uniform heat distribution, greatly reduced chance of combustion, faster warm up time, greater portability, greater ease of use, and simplification of manufacture.

SUMMARY OF THE INVENTION

Applicant's invention uses forced convective heating to heat the tobacco, thereby producing the most uniform distribution of heat. Uniform temperature distribution means that all areas of the tobacco will be relatively close to the same temperature, thus avoiding the problem of overheating some areas while underheating others. This helps to get most complete use of the tobacco, without overheating any one part.

Applicant's invention also uses a temperature limiting system which keeps the temperature safely below the temperature of spontaneous combustion of plant material, whereas other devices allow the user to overheat and combust the source material.

Applicant's invention uses a lightweight heating element that can rapidly warm up to operating temperature, meaning the user does not have to wait for many minutes just for the heating element to warm up.

Applicant's invention is substantially smaller and more portable than prior art devices. Most prior art devices plug into the wall for power, which basically requires that those devices be used indoors, or at least somewhere where there is access to AC power. Applicant's invention is battery powered, which means it can be used anywhere.

Applicant's device comprises a power switch but no temperature or heating adjustment, with the temperature automatically limited to just under combustion temperature by the internal temperature control module. This is much simpler than other devices that have settable temperature or heating controls, which require the user to determine, through a process of trial and error, the optimal setting. Still other devices, which do not have settable temperature or heating controls, nonetheless require the user to learn at what rate to suck air through the tobacco, and have likened the skill necessary to that of playing a musical instrument.

Applicant's invention, by using forced convective heating, controls both the temperature and the flow rate through the tobacco, making the device as simple to use as possible for the user, who can inhale at whatever rate he/she likes from the mouthpiece (inhalation) tube, without influencing the flow rate through the tobacco. This results because the mouthpiece tube is formed to include an aperture to allow cool air to mix in with the mist or condensation aerosol which is actively pumped out of the tobacco chamber, and into the mouthpiece tube.

Applicant's temperature limiting system is less expensive to manufacture than a precise temperature controller. In addition, Applicant's apparatus does not require, and does not comprise, a large thermal mass.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
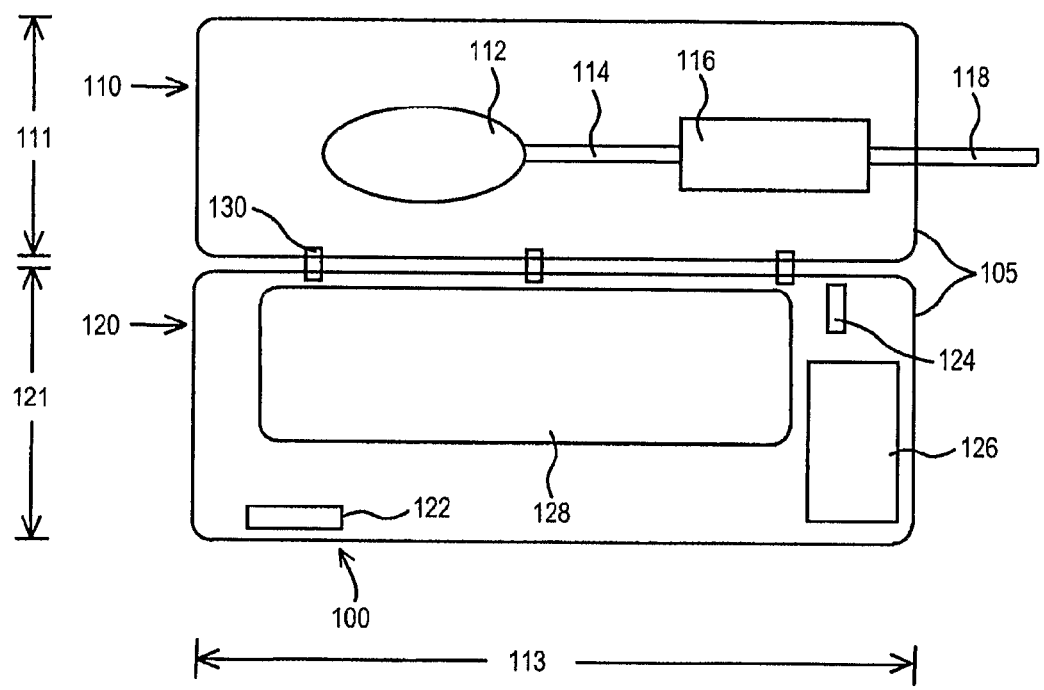
FIG. 1 shows a top view of the two halves of the preferred embodiment of the device.

Referring now to FIG. 1, Applicant's apparatus 100 comprises a housing 105. In certain embodiments, that housing 105 comprises a top portion 110 hingedly interconnected by a plurality of hinges 130 to a bottom portion 120.

In certain embodiments, apparatus 100 weighs between about 6 ounces and about 16 ounces. In certain embodiments, apparatus 100 weighs 14 ounces.

Top portion comprises a width 111 and a length 113. Top portion 110 is formed from a rigid material, such as for example wood, metal, plastic, and combinations thereof. In certain embodiments, width 111 is between about 2 inches and about 3 inches. In certain embodiments, width 111 is 2.75 inches. In certain embodiments, length 113 is between about 5 inches and about 6.5 inches. In certain embodiments, length 113 is 6 inches.

Bottom portion 120 comprises width 121, and length 113. In certain embodiments, width 121 is between about 2 inches and about 3 inches. In certain embodiments, width 121 is 2.75 inches. Bottom portion 120 is formed from a rigid material, such as for example wood, metal, plastic, and combinations thereof.

When apparatus 100 is placed in a closed configuration, i.e. portion 110 is rotated inwardly about 180 degrees around hinges 130, that closed configuration comprises a thickness of between about 1.25 inches and about 2.25 inches. In certain embodiments, that thickness is 1.75 inches.

A metal box is preferred, because this has less chance of melting or catching fire in the event of a malfunction of the device, and is less breakable if dropped. In certain embodiments, top portion 110 and bottom portion 120, and plurality of hinges 130 comprise an integrally molded enclosure comprising an engineering thermoplastic such as one or a combination of the following would also be suitable as the box material: Polysulfone (PSU), Polyethersulfone (PES), Polyetherimide (PEI), Polyarylate resins, Polyetheretherketone (PEEK™), or polyphenylene oxide.

In the illustrated embodiment of FIG. 1, top portion 110 comprises air pump 112, which pumps air through a heating element assembly 114 to an insulating block 116, which interconnects heating element assembly 114 with removable mouthpiece tube 118. Lower portion 120 comprises power switch 122, a safety switch 124, a temperature control module 126, and a battery pack 128.

In certain embodiments, air pump 112 comprises a fan or blower. In other embodiments, air pump 112 comprises a diaphragm pump. In yet other embodiments, air pump 112 comprises a vane pump. Diaphragm pumps or vane pumps are preferable because they generate sufficient pressure in addition to a certain volume of airflow. Applicant has found that diaphragm pumps, such as the kind used in automatic inflation blood pressure monitors, are well suited for this application because that pump motor draws little energy from battery pack 128.

Applicant has further discovered an additional advantage of a diaphragm pump or vane pump over a fan, namely the air flow rate does not vary as a result of output restriction. Therefore, the heating energy produced by heating element 310 (FIG. 3) does not need to be adjusted based on flow rate. If the air flow rate varied, however, then the heating control system would need to adjust for this. Moreover, with Applicant's low thermal mass heating element, a constant gas flow enables a more uniform and constant heating over repeated uses, and reduces the time necessary to attain a stable temperature.

In selecting the ideal air flow rate, several factors were taken into account. One factor, for example, comprises the average amount of air inhaled by a person in one breath. This is called in medical terminology the "tidal volume" and is approximately 0.5 liters. This is the volume of a normal breath, not a deep breath, or an intentionally shallow breath. Applicant used this quantity of air as the target quantity of air plus smoke or vapor that one would inhale when inhaling from a smoking device, such as a pipe or cigarette.

A second factor comprises the percentage of an inhaled breath that is inhaled from the cigarette or pipe, which is usually about 50%. A breath in which one inhales purely cigarette smoke would contain more smoke particles than most user's lungs can handle, and would cause the lungs to reject it by coughing. Furthermore, the smoke produced by a lit cigarette is very hot, and smokers therefore mix cool air with the smoke when inhaling. As a result, smokers do not generally inhale an entire lungful of dense cigarette smoke directly through the cigarette.

Yet a third factor comprises the number of breaths per minute the average person takes. The typical resting adult breathing pattern is a breathing rate of 10-20 breaths per minute, with ⅓ of the breath time in inspiration. This therefore yields an average tidal volume per minute estimate of between 5 and 10 liters.

As those skilled in the art will appreciate, it is desirable that the vapor be delivered at a rate not faster than the rate that the user can comfortably inhale, considering the mixing in of cooling air. Apparatus 100 achieves a balance between the rapidity of vaporization, which would increase the energy required and also increase the size of the air pump, and possibly increase the waste or unused vapor if it is produced at a rate greater than what the user can comfortably inhale, and the desire to mimic the production of vapor realized from a conventional cigarette. Applicant has determined experimentally that a flow rate of approximately 1 Liter per minute of vapor (condensation aerosol) can comfortably be breathed in, mixed with ambient air, and allow the user to still get sufficient oxygen from the air, and also gain the benefits of the inhaled vapor.

Apparatus 100 pumps air through the source material chamber 210 (FIGS. 2, 3) regardless of the packing density of the source material disposed in that chamber. Human lungs are capable of generating a vacuum of 2 mm Hg, (0.04 psi). Therefore, in certain embodiments, Applicant's air pump 112 provides air at a pressure of at least 0.04 psi to Applicant's heating element assembly 114, thereby pumping air through a tobacco-filled source material chamber 210, even if that source material chamber is packed so tightly that a user can just barely suck air through it. Those of skill in the art will appreciate that for ideal vaporization the source material should preferably be shredded to a relatively constant size and density, similar to that in cigarettes. Apparatus 100 functions optimally throughout a range of source material packing densities.

Power switch 122 turns on power to the unit. In certain embodiments, switch 212 comprises a single throw/double pole electrical switch. In other embodiments, switch 122 comprises an electronic switch. In certain embodiments, switch 122 operates both the heating element and the air pump. In other embodiments, switch 122 comprises an electronic switch which causes the heating control unit to preheat the heating element before turning on the air pump.

In certain embodiments, control module 126 comprises a timer that automatically shuts off both the heating element and the air pump after a pre-determined number of minutes as a safety feature in the event the user forgets to turn the unit off. In certain embodiments this automatic shut-off feature can be disabled to place apparatus 100 temporarily into "incense mode" such that if the user is vaporizing a small block of incense for room odorizing, that the unit would stay on for a much longer period of time (e.g. 30 min.) before automatically shutting off.

In certain embodiments, safety switch 124 comprises a pin switch that interrupts power to the heating element assembly and to the air pump when top portion 110 is closed against bottom portion 120. This is a safety feature, because apparatus 100 is intended only for use in the open position.

The temperature control module 126 comprises circuitry interconnected with temperature sensor 350 (FIG. 3) to monitor the temperature of the output air from the heating element tube, and regulate the power to the heating element so as not to allow it to get so hot as to cause the source material to spontaneously combust. In certain embodiments, Applicant's circuitry comprises a closed loop control circuit, which uses pulse width modulation to regulate the power to the heating element. Applicant's circuitry comprises a throttling or limiting circuit, because it initially allows as much current to flow through the heating element as the batteries or power supply will deliver, but throttles this current flow as the temperature approaches a 450° F. temperature threshold.

In certain embodiments, Applicant's circuitry uses a thermocouple as the temperature sensor coupled with a cold junction compensator chip and an amplifier to bring the voltage of the thermocouple to adequate voltage to work in the closed loop controller chip. For the closed loop controller chip, in this embodiment Applicant utilizes a CLOZD™ (Caldwell Loop Optimization in Z-Domain) loop controller chip, from Flextronics, of Carlsbad, Calif. In other embodiments, Applicant's circuitry comprises a microprocessor running a feedback control program.

Apparatus 100 needs approximately 20 Watts of power to operate. In certain embodiments, battery pack 128 comprises an 8 AA NiMH (nickel metal hydride) rechargeable battery pack. This provides 9.6 V, and up to 5 A of current. In other embodiments, a lithium battery pack is used. In other embodiments, apparatus 100 comprises a plug so that a wall transformer can be plugged in to both power the unit and charge the batteries, not necessarily both at the same time. In certain embodiments, apparatus 100 further comprises a smart charging circuit so the device can be left plugged in indefinitely and will be fully charged and ready to use whenever desired.

In certain embodiments, wall power is used either to charge the batteries, or to supply power to operate the unit in case the batteries were discharged. In other embodiments, a power supply which can supply the current necessary to both charge the batteries at the same time as providing the current necessary to operate the device is used.

Figure 2:
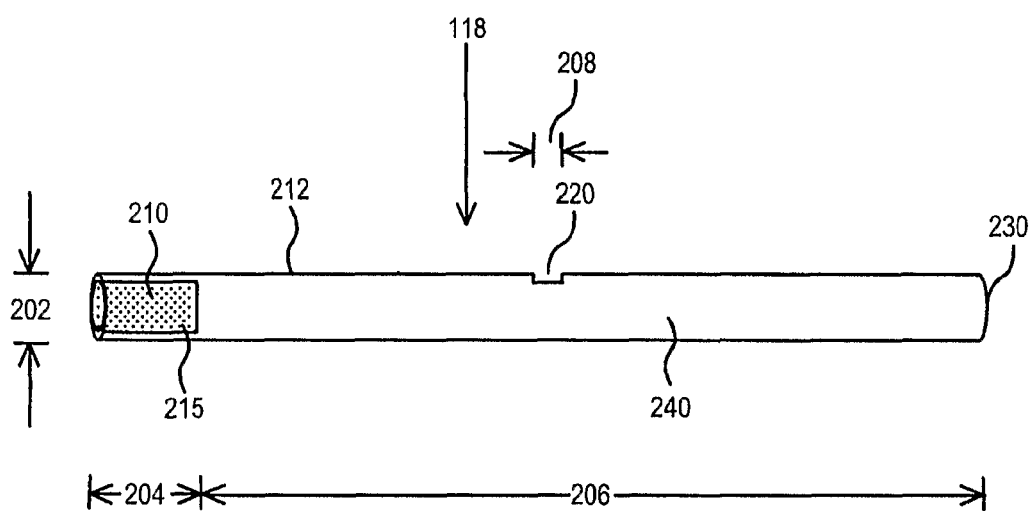
FIG. 2 shows Applicant's mouthpiece tube.

Referring now to FIG. 2, mouthpiece tube 118 comprises a tubular source material chamber 210, screen 212, and tubular member 240 which comprises output end 230. The user inhales vapors from output end 230.

In certain embodiments, source chamber 210 comprises a PYREX tube. Source chamber 210 comprises diameter 202 and length 204. In certain embodiments, diameter 202 is between about 4 mm and about 12 mm. In other embodiments, diameter 202 is approximately 8.7 mm, selected such that it will optimally hold a short piece (whose length matches that of the length of the source material chamber) of a standard sized cigarette, which can be cut off from a cigarette by the user and inserted. In certain embodiments, diameter 202 is 7 mm. In certain embodiments, length 204 is between about 5 mm and about 15 mm. In certain embodiments, length 204 is 10 mms.

Tubular member 240 comprises diameter 202 and length 206. Tubular member 240 is formed from one or more rigid materials, such as for example wood, metal, plastic, glass, PYREX, and combinations thereof. In certain embodiments, length 206 is between about 2 inches and about 4 inches. In certain embodiments, length 206 is 3 inches.

In the illustrated embodiment if FIG. 2, tubular member 240 is formed to include aperture 220 comprising diameter 208. Aperture 220 allows cool ambient air to mix with the air stream of vaporized compounds upon inhalation. In certain embodiments, diameter 208 is between about 2 mm and about 6 mm. In certain embodiments, diameter 208 is 4 mm.

In certain embodiments, mouthpiece tube 118 comprises a PYREX tube. Cooling air inlet aperture 220 allows ambient air to mix with the vapor produced by the device so that the user does not inhale the 400+ degree air coming from the hot source material. The active ingredients are thus inhaled as a condensation aerosol or mist.

The hot air flowing through the tobacco contained in the source material chamber 210 vaporizes the compounds which have boiling or vaporization temperatures at or below the incoming air temperature (at 1 Atm air pressure). When the compounds change phase from liquid (they are generally considered oils) to gas, they absorb heat energy. This energy is called the "heat of vaporization." These compounds then condense into liquid form (tiny droplets) in the moving air stream.

When the volatilized compounds condense to form an aerosol, they release the heat of vaporization energy back into the air around them. This is another reason why Applicant has selected the air flow rate described above. If this condensation takes place relatively close to the place of initial vaporization, then the released heat can be recycled to vaporize more of the compounds of interest (repeat the process). This leads to the most efficient use of heat energy, which is of utmost importance in this invention, since it is primarily intended to be battery powered, and therefore has a finite supply of energy to use.

Screen 212 prevents particles of tobacco from being inhaled by the user. Screen 212 comprises diameter 212. In certain embodiments, screen 212 is formed from one or more metals, such as for example brass, steel, and the like. In other embodiments, screen 212 is formed from one or more ceramic materials.

Figure 3:
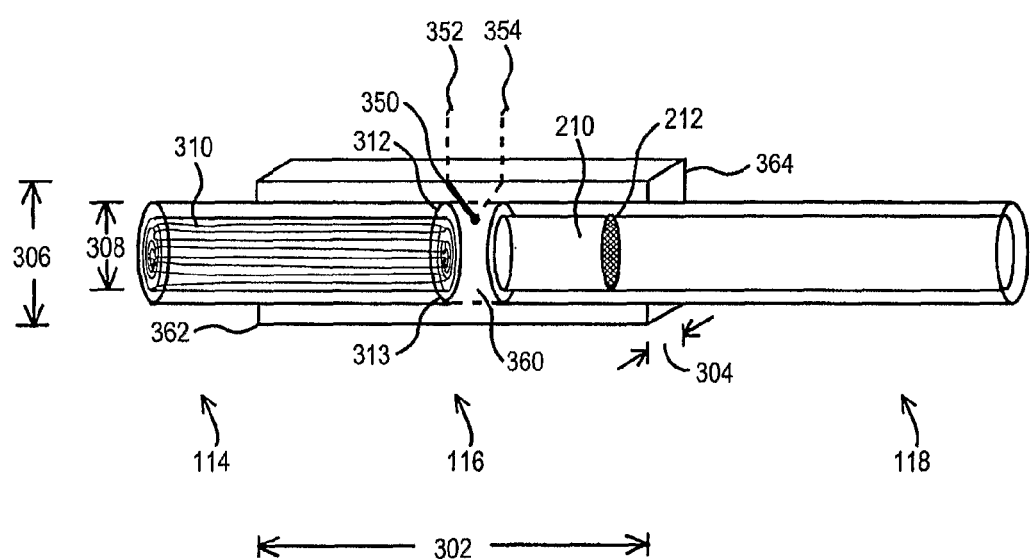
FIG. 3 shows Applicant's insulating block in combination with the mouthpiece tube and the heating element tube.

Referring now to FIG. 3, insulating block 116 comprises length 302, width 304, and height 306. In certain embodiments, length 302 is between about 0.75 inches and about 2.5 inches. In certain embodiments, length 302 is 1.5 inches. In certain embodiments, width 304 is between about 0.5 inch and about 1.25 inches. In certain embodiments, width 304 is 0.75 inch. In certain embodiments, height 306 is between about 0.5 inch and about 1.25 inches. In certain embodiments, height 306 is 0.75 inch.

Insulating block 116 further comprises a tubular structure having a first open end 362 and a second open end 364 interconnected by lumen 360. In certain embodiments, lumen 360 comprises diameter 308. In certain embodiments, insulating block 116 is formed from wood, because wood provides good heat insulation. In other embodiments, insulating block 116 is formed from ceramic, i.e. porcelain or clay. With a wood insulating block, Applicant has determined that while the air flowing out of the heating element assembly 114 was over 400 degrees Fahrenheit, even after 12 minutes, the outside of the insulating block 116 remained at less than 200 degrees Fahrenheit.

Heating element assembly 114 comprises heating element 310. Heating element assembly 114 is inserted into lumen 360 through first open end 362. Screen 312 prevents loose tobacco contained in the source material chamber 210 from contacting the heating element 310. Temperature sensor 350 is located between the output end 313 of heating element assembly 114 and mouthpiece tube 118. In certain embodiments, heating element assembly 114 comprises a PYREX tube containing a coiled nichrome wire heating element 310 disposed therein. PYREX is a registered trademark owned by Corning Incorporated, One Riverfront Plaza, Corning N.Y. 14831.

The nichrome heating element 310 comprises a resistance of approximately 3-5 Ohms. Nichrome wire is well suited for this application because of its constant resistance over a large temperature range. Therefore, a change in resistance of the heating element 310 with temperature is not a factor to be included in the design of the temperature controller 126.

In certain embodiments, heating element assembly 114 comprises a tubular structure comprising walls having a thickness of about 2 mm. In addition, heating element assembly 114 comprises a weight of about 6 grams. Forming heating element assembly 114 with thin walls and a minimal weight wastes as little heat as possible heating the mass and walls of the tube 114 thereby conserving as much heat as possible for use in vaporizing the desired compounds. In addition, by forming these chamber walls as small as possible, this also helps the device warm up to temperature faster. In certain embodiments, heating element assembly 114 comprises a weight of about 6 grams.

As those skilled in the art will appreciate, the light weight of heating element assembly 114 translates into a small thermal mass. Because of this small thermal mass, heating element assembly 114 rapidly heats such that Applicant's apparatus 100 begins vapor production in about 10 seconds after energizing the heating element 310. This being the case, the user can begin to inhale nicotine and other flavors after about 10 seconds, though the flavors tend to come off earlier, and the nicotine somewhat later, because nicotine has a higher vaporization temperature. In certain embodiments, heating element assembly 114 reaches seventy-five percent (75%) of full operating temperature in 15 seconds, ninety percent (90%) of full operating temperature in 30 seconds, and stable (+/−5° F.), full operating temperature in 60 seconds.

Mouthpiece tube 118 is removeably disposed in lumen 360 through second open end 364. The mouthpiece tube is removable. In use, source material chamber 210 is located immediately adjacent to the output end 313 of the heating element assembly 114. End 313 of the heating element tube and source material chamber 210 are almost touching to ensure that the hot air produced by the heating system flows directly into and through the source material, thus making the most efficient use of the supplied heat energy.

In certain embodiments, apparatus 100 further comprises a flexible clear plastic tube attached to the end of the mouthpiece tube. Such a tube collects the generated aerosol so that the user could inhale a larger quantity in a single breath than the amount which accumulates in the relatively short source material tube. In addition, such a tube, allows the aerosol to cool to a comfortable and non-dangerous inhalation temperature. Moreover, such a tube gives the user a visual confirmation of aerosol generation.

In certain embodiments, this flexible tube comprises heat resistant, medical grade, clear tubing. The advantage of using this tube as a vapor collection device is that the user can find similar tubes readily available in a hardware store, and cut the tube to the desired length. The longer the tube, the more vapor it will hold. This allows the user to inhale a significant quantity of cooled vapor in one rapid breath, rather than inhaling the same amount of vapor in many separate breaths, directly from the end of the mouthpiece tube. The tube will also make it easier to observe the presence of vapor, since this can be difficult to see, because it is much finer and less dense than ordinary smoke.

To use the device, the user fills the source material chamber with some appropriately ground tobacco, opens the device, and inserts the mouthpiece tube into the insulating block. In certain embodiments, the user can cut a short piece from the cigarette of his/her choice, and insert this piece into the source material chamber, and then insert the mouthpiece tube into the insulating block. Then the user simply turns the power switch on, and inhales from the mouthpiece end of the mouthpiece tube. This is continued as long as the user continues to receive active ingredients and flavor compounds. With experience, the user will be able to tell when all the volatile compounds in the tobacco have been vaporized, (much like smoking from a pipe, and knowing by taste that all the tobacco has turned to ash) and can then turn the unit off and repeat the process.

While the preferred embodiments of the present invention have been illustrated in detail, it should be apparent that modifications and adaptations to those embodiments may occur to one skilled in the art without departing from the scope of the present invention.

I claim:

1. A method to produce a condensation aerosol from a solid source material disposed in an hand-held apparatus, comprising the steps of:

supplying a hand-held apparatus comprising a mouthpiece tube, a source material chamber in communication with said mouthpiece tube, a heating element assembly weighing about 6 grams in communication with said source material chamber, a temperature sensor to monitor the temperature of output air from said heating element, a temperature control module interconnected to said temperature sensor, and an air pump in communication with said heating element assembly;

disposing a solid source material in said source material chamber;

energizing said air pump;

energizing said heating element assembly, wherein said temperature control module regulates the power provided to said heating element, and wherein said temperature control module throttles current flow to said heating element as the temperature of said output air approaches 450° F.;

providing ambient air from said air pump to said heating element assembly;

providing heated air from said heating element assembly to said source material chamber;

convectively heating said source material using said heated air;

vaporizing one or more volatile compounds disposed in said solid source material;

emitting from said mouthpiece tube a condensation aerosol comprising said one or more volatile compounds.

2. The method of claim 1, wherein said emitting step further comprises emitting from said mouthpiece tube at a flow rate of 1 liter per minute a condensation aerosol comprising said one or more volatile compounds.

3. The method of claim 1, wherein:
said supplying step further comprises supplying a hand-held device comprising a power source.

4. The method of claim 1, wherein said heating element assembly comprises a heating element, and wherein said energizing said heating element assembly step further comprises:

providing power to said heating element;
providing power to said air pump;
increasing the temperature of said heating element to an operating temperature of 450° F. plus or minus 5° F. in about 60 seconds.

5. The method of claim 4, wherein said increasing the temperature step further comprises:

reaching seventy-five percent (75%) of said operating temperature in 15 seconds;
reaching ninety percent (90%) of said operating temperature in 30 seconds.

6. The method of claim 4, wherein said providing ambient air step further comprises ambient air from said air pump to said heating element assembly at a pressure of at least 0.04 psi.

7. The method of claim 6, wherein said supplying step further comprises providing a hand-held device comprising:

a top portion hingedly attached to a bottom portion;
a safety switch interconnected with said control module;
said method further comprising the steps of:
determining by said safety switch if said top portion is closed against said bottom portion;
operative if said top portion is closed against said bottom portion, discontinuing the supply of power to said heating element and to said air pump.

* * * * *